United States Patent [19]
Tatterson et al.

[11] Patent Number: 5,530,151
[45] Date of Patent: Jun. 25, 1996

[54] METHOD OF PASSIVATING ORGANOCHLOROSILANE REACTOR FINES AND SALVAGING CHLOROSILANE VALUES THEREFROM

[75] Inventors: Robert L. Tatterson; Larry A. Divins, both of Clifton Park; Robert G. Stank, Ballston Spa, all of N.Y.

[73] Assignee: General Electric Company, Schenectady, N.Y.

[21] Appl. No.: 494,039

[22] Filed: Jun. 26, 1995

[51] Int. Cl.⁶ .............................. C07F 7/16; C01B 33/08
[52] U.S. Cl. ..................... 556/472; 423/324; 423/342; 502/56
[58] Field of Search ..................... 556/472; 423/342, 423/324; 502/56

[56] References Cited

U.S. PATENT DOCUMENTS

| | | | |
|---|---|---|---|
| 4,390,510 | 6/1983 | Ritzer et al. | 423/342 |
| 4,500,724 | 2/1985 | Ward, III et al. | |
| 4,824,652 | 4/1989 | Hosokawa | 423/324 X |
| 5,274,158 | 12/1993 | Webb et al. | |

*Primary Examiner*—Paul F. Shaver
*Attorney, Agent, or Firm*—William H. Pittman

[57] ABSTRACT

Silicon fines which have been recovered from an organochlorosilane reactor are treated with HCl or elemental chlorine at an elevated temperature to salvage chlorosilane and metal salt values. Passivation is also achieved.

8 Claims, No Drawings

METHOD OF PASSIVATING ORGANOCHLOROSILANE REACTOR FINES AND SALVAGING CHLOROSILANE VALUES THEREFROM

BACKGROUND OF THE INVENTION

The present invention relates to a process for simultaneously passivating organochlorosilane reactor fines and generating values therefrom.

As shown in U.S. Pat. No. 4,500,724, methylchlorosilane reactor fines (hereinafter sometimes "silicon-containing fines") may be generated during the synthesis of methylchlorosilanes by the reaction of powdered silicon with methyl chloride, usually in the presence of a copper catalyst. Some of the generated fines are recycled, while others are discarded. As discussed in U.S. Pat. No. 5,274,158, a serious discarded fines management problem can occur with respect to build-up and disposition, as these materials are often pyrophoric. Silicon-containing fines can have an average particle size of about 0.1 to about 200 microns with at least 2% copper by weight in the elemental or chemically combined state.

As shown in the aforementioned U.S. Pat. No. 5,274,158, a procedure which can be used to render pyrophoric silicon-containing fines substantially non-reactive in air is to subject them to a heat treatment in an inert atmosphere at a temperature in the range of about 900°–1500° C.

Early studies also showed that $SiCl_4$ and $HSiCl_3$ can be made by contacting metallurgical grade silicon powder and HCl in the presence of a copper catalyst at about 300° C. Higher temperature are known to favor the exclusive formation of $SiCl_4$. Although various procedures are known for passivating discarded silicon-containing fines to render them more manageable, interest also has been shown in developing techniques for both salvaging and passivating silicon-containing fines to derive some of the silicon and metallic values from the discarded finely divided silicon contact mass.

SUMMARY OF THE INVENTION

The present invention is based on the discovery that contact between silicon-containing fines which would otherwise be discarded and HCl or elemental chlorine at a high temperature simultaneously generates metallic values and passivates silicon from such discarded reactor fines.

Accordingly, the invention is a treatment method for salvaging metallic values and passivating silicon from silicon-containing fines resulting from the reaction of silicon powder with hydrogen chloride or an organic chloride, said method comprising contacting said fines with HCl or elemental chlorine at a temperature in the range of about 500°–1200° C. to form a mixture comprising silicon chlorides and metallic salts.

DETAILED DESCRIPTION OF THE INVENTION

Silicon chlorides which can be generated and salvaged in accordance with the practice of the invention are primarily $SiCl_4$ and $HSiCl_3$. Among the metal chlorides which can be salvaged, there are included chlorides of copper, zinc and tin.

The silicon-containing fines to be treated in accordance with the method of the invention include materials shown in U.S. Pat. Nos. 4,724,122 and 5,000,934. They typically have a particle size in the range of about 0.1–200 microns and a surface area of up to about 25 m²/g.

In the practice of the invention, fines recovered, for example, from a fluidized bed organohalosilane reactor, which fines can be stored in a hopper under nitrogen, can be fed into a reactor such as a rotary kiln under batch, semi-batch, or continuous conditions. The fines may be agitated, ordinarily for a period of 1–3 hours, in an HCl or chlorine atmosphere. HCl can be employed, for example, at 0.1–3.0 atmospheres pressure and can be utilized in combination with an inert gas such as nitrogen or helium if desired. Treatment temperatures are in the range of 500°–1200° C.

It is frequently possible, in accordance with the invention, to recover essentially all the silicon present in the fines as valuable silicon chlorides, predominantly silicon tetrachloride. Moreover, copper and other metals present are typically converted to high purity chlorides which are also capable of further use.

In preferred embodiments of the invention, the HCl contact is effected in a first reaction zone and the product thereof is conveyed to one or more zones in which later stages are conducted. These can include a first heat exchange and separation zone employing a vessel having means for heat recovery resulting in steam generation, in which vessel recovery of metal salts, silicon chlorides and passivated contact mass residue, which may include as silicon oxides, silicon carbides and copper silicates, may be achieved. A second heat exchange and steam generation zone in a second similar vessel also can be used if necessary to allow a final stripping operation performed on the product of said first heat exchange and separation zone, for recovery of silicon chlorides and passivated silicon contact mass. Said passivated silicon contact mass is typically substantially nonreactive in air at temperatures to 350° C.

The following examples illustrate the practice of the invention.

EXAMPLE 1

A mixture of 0.1 atm. of HCl and 0.9 atm. of helium was passed over 30 mg of silicon-containing fines recovered from a methylchlorosilane reactor. The fines were in a platinum pan at 900° C. The weight loss of the fines was measured over about a five-hour period. Processing of the fines in the HCl atmosphere resulted in a rapid and substantial weight loss within about 1.5 hours. This was due to conversion to metal chlorides and chlorosilanes. About 1.0% initial weight was lost due to absorbed water.

The above procedure was repeated, except that the fines were processed in a helium atmosphere. It was found that the fines experienced no significant loss of weight except for loss due to absorbed water.

Processed and unprocessed fines were then examined for oxygen reactivity by passing a dilute air mixture over the samples at 300° C. The fines processed at 900° C. showed no weight gain, while weight gain due to formation of metal oxides was observed with unprocessed fines.

EXAMPLE 2

Thirty grams of silicon-containing fines recovered from a methylchlorosilane reactor were heated at 300° C. in a quartz reaction tube under flowing helium to remove any absorbed water. After the silicon-containing fines sample was dry, a condenser system was attached. HCl was introduced into the reactor and the temperature was raised to 900°

C. The fines were treated for five hours followed by cooling the furnace under a helium purge.

Although less than one gram of liquid was collected, greater quantities were formed as shown by buildup of a white siloxane residue in a water scrubber. As shown by gas chromatography, the liquid condensate was 95 wt % $SiCl_4$ and the balance $HSiCl_3$. A possible explanation of not retrieving the balance of liquid silanes generated was an inefficient condensation system and poor gas-solid interaction.

The above procedure was repeated at 300° C. for 6.5 hours. No liquid condensate was collected and a loss of 0.18 g of fines resulted.

Subsequent testing of the fines treated at 300° C. and 900° C. also showed significant passivation with respect to evolved hydrogen gas after being mixed with a water-surfactant mixture. Untreated fines generated 700 ml of evolved hydrogen per 10 g of sample, as compared with treatment at 300° and 900° C. which generated 181 and 130 ml, respectively.

What is claimed is:

1. A method for salvaging metallic values and passivating silicon from silicon-containing fines resulting from the reaction of silicon powder with hydrogen chloride or an organic chloride, said method comprising contacting said fines with HCl or elemental chlorine at a temperature in the range of about 500°–1200° C. to form a mixture comprising silicon chlorides and metallic salts.

2. A method in accordance with claim 1 where the recovered silicon chlorides are a mixture of $SiCl_4$ and $HSiCl_3$.

3. A method in accordance with claim 1 where the silicon fines result from a reaction between methyl chloride and silicon powder in presence of a copper catalyst.

4. A method in accordance with claim 1 where the silicon fines are treated with a mixture of HCl and an inert gas.

5. A method in accordance with claim 1 where said mixture is produced in a first reaction zone and the product thereof is conveyed to a first heat exchange and separation zone to effect recovery of heat and separation of metallic salts.

6. A method in accordance with claim 5 where the product of said first heat exchange and separation zone is conveyed to a second heat exchange zone to separate volatile silicon chlorides and recover a passivated silicon-containing contact mass which is substantially nonreactive in air at temperatures to 350° C.

7. A continuous method in accordance with claim 1.

8. A batch method in accordance with claim 1.

* * * * *